US005980452A

United States Patent [19]

Garenfeld et al.

[11] Patent Number: 5,980,452

[45] Date of Patent: Nov. 9, 1999

[54] HAIR REMOVAL APPLIANCE WITH ADJUSTABLE HAIR EXTRACTION DISTANCE

[75] Inventors: Andreas J. Garenfeld; Petrus H. De Leeuw; Gerardus Van Veen; Paul A. Ackermans; Peter E. Wierenga, all of Eindhoven, Netherlands

[73] Assignee: U.S. Philips Corporation, New York, N.Y.

[21] Appl. No.: 08/906,497

[22] Filed: Aug. 5, 1997

[30] Foreign Application Priority Data

Aug. 16, 1996 [EP] European Pat. Off. .............. 96202303

[51] Int. Cl.[6] ........................ A61B 17/50

[52] U.S. Cl. ........................ 600/133; 30/34.2

[58] Field of Search ........................ 30/34.2, 34.3, 30/43.1; 606/1, 131, 133; 452/80, 81, 83, 100

[56] References Cited

U.S. PATENT DOCUMENTS 3,088,205 5/1963 Ellis ........................ 30/34

FOREIGN PATENT DOCUMENTS

0532106 B1 3/1993 European Pat. Off. .
2424109 11/1979 France .

*Primary Examiner*—Glenn K. Dawson
*Attorney, Agent, or Firm*—Ernestine C. Bartlett

[57] ABSTRACT

An appliance for removing hairs growing from skin is provided with a clamping device and a cutting device cooperating therewith. The clamping device clamps the hairs to be removed and subsequently extracts them at least partly from the skin, whereupon the hairs extracted partly from the skin are cut through adjacent the skin by the cutting device. The hairs thus cut through return to below the surface of the skin, so that a smooth shaving result is achieved which remains intact during a considerable period. According to the invention, the appliance is provided with structure for adjusting an extraction distance over which the clamping device extracts the hairs from the skin before they are cut through by the cutting device. In a special embodiment, the structure is adjustable to a first mode in which the appliance purely has a shaving function and to a second mode in which the appliance purely has a depilation function.

15 Claims, 6 Drawing Sheets

HAIR REMOVAL APPLIANCE WITH ADJUSTABLE HAIR EXTRACTION DISTANCE

BACKGROUND OF THE INVENTION

The invention relates to an appliance for the removal of hairs growing from skin, which appliance is provided with a clamping device for clamping a hair and subsequently extracting the hair at least partly from the skin, and with a cutting device for cutting through, adjacent the skin, of a hair which has been partly extracted from the skin.

An appliance of the kind mentioned in the opening paragraph is known from U.S. Pat. No. 3,088,205. The known appliance comprises a comb-shaped cutting member capable of oscillation and provided with a row of cutter elements. The cutter elements of the cutting member bear on a foil which is provided with hair trap openings. The cutting member further comprises a clamping element arranged on either side of each cutter element in a fixed position relative to the cutting member, for example a flexible metal strip or a rubber strip. A hair penetrating one of the hair trap openings during operation is first clamped between the foil and one of the clamping elements, the hair being extracted partly from the skin as a result of the movement of the clamping element relative to the foil. The hair is subsequently cut through owing to a cooperation between a cutter element adjoining the relevant clamping element and an edge of the relevant hair trap opening, a portion of the hair clamped in between the foil and the clamping element being cut off. Since the hair shortened in this manner is no longer clamped in, the shortened hair returns into the skin, the end of the shortened hair sinking to below the surface of the skin. A smooth shaving result is thus achieved through the use of the clamping elements, the skin also remaining smooth for a reasonably long period after shaving.

A disadvantage of the known appliance is that the process of partly extracting the hairs from the skin before they are cut through is somewhat painful. The removal of hairs by means of the known appliance is more painful as a result of this than is the removal of hairs by means of a shaver which is usual and known per se and which performs exclusively a cutting action. The user of the known appliance has no degree of choice. The user will normally achieve a smoother shaving result with the known appliance than with a shaver having a cutting action only, but the removal of hairs by means of the known appliance is always painful to a certain extent.

SUMMARY OF THE INVENTION

It is an object of the invention to provide an appliance of the kind mentioned in the opening paragraph with which the above disadvantages of the known appliance are avoided as much as possible.

The appliance according to the invention is for this purpose characterized in that the appliance is provided with means for adjusting an extraction distance over which the clamping device extracts the hair from the skin before the cutting device cuts through the hair. The fact that the appliance according to the invention comprises said means enables the user of the appliance to adjust the extraction distance over which the clamping device extracts the hairs from the skin before they are cut through by the cutting device. This affords the user a freedom of choice. The user may set, for example, a comparatively short extraction distance, which does provide a less smooth shaving result but renders the removal of the hairs substantially painless, or set a comparatively great extraction distance, which does achieve a very smooth shaving result which remains intact during a comparatively long period but leads to a comparatively painful hair removal process. Alternatively, the user may, for example, set an average value for the extraction distance, which achieves a good smoothness which remains intact for a reasonable period and which is accompanied by an acceptable pain level.

A special embodiment of an appliance according to the invention is characterized in that the means for adjusting the extraction distance are adjustable at least to a first setting in which the extraction distance is zero or substantially zero and to a second setting in which the clamping device extracts the hairs completely from the skin. In this special embodiment, the appliance has a wide application range. In the first setting, the hairs are not or substantially not extracted from the skin before they are cut through by the cutting device, so that the appliance exclusively has a painless cutting action. In the second setting, the appliance has a depilation function, the hairs being extracted completely from the skin. In addition, said means may be, for example, continuously adjustable between the first and the second setting, so that the user may select any desired result between a maximum smoothness and a maximum time during which the smoothness is retained, achieved with comparatively much pain in the second setting, and a minimum smoothness and a minimum time during which this smoothness is retained, achieved in the first setting without pain. The user may also, for example, use the appliance first in the first setting for shortening long hairs and subsequently in the second setting for depilating the previously shortened hairs.

A further embodiment of an appliance according to the invention is characterized in that the clamping device comprises at least one clamping element which is movable relative to a hair trap opening of the appliance, the means for adjusting the extraction distance comprising means for adjusting a clamping force with which the clamping device clamps the hair. The clamped hairs are extracted from the skin in this embodiment as a result of the movement of the clamping element relative to the hair trap opening. If a comparatively strong clamping force is set with the means for adjusting the clamping force, comparatively little slip will occur between the movable clamping element and the clamped hairs, so that the clamped hairs will be carried along over a comparatively long distance by the movable clamping element, and a comparatively great extraction distance is achieved. If a comparatively weak clamping force is set with the means for adjusting the clamping force, comparatively much slip will occur between the movable clamping element and the clamped hairs, so that the clamped hairs will be carried along over a comparatively short distance by the movable clamping element, and a comparatively small extraction distance will be achieved. The extraction distance is thus rendered adjustable in a simple manner.

A yet further embodiment of an appliance according to the invention is characterized in that the clamping device comprises at least one pair of cooperating clamping elements which are movable relative to a hair trap opening of the appliance, the means for adjusting the extraction distance comprising means for adjusting a position of the cutting device relative to the clamping device. The hairs are clamped between the cooperating clamping elements adjacent the hair trap opening in this embodiment and extracted from the skin as a result of the movement of the cooperating clamping elements relative to the hair trap opening. The position in which the clamped hairs are cut through is determined by the selected position of the cutting device relative to the clamping device. The extraction distance over which the clamping device extracts the hairs from the skin before they are cut through by the cutting device is determined by a distance between said position in which the hairs are cut through and a position in which the hairs are clamped by the clamping elements. Since the position in which the hairs are cut through is adjustable through adjustment of the position of the cutting device relative to the clamping device, the extraction distance can be adjusted in a simple manner through adjustment of said position of the cutting device.

A special embodiment of an appliance according to the invention is characterized in that the clamping device is provided with a carrier which is rotatable about an axis of rotation directed parallel to the hair trap opening and which is provided with an elastic clamping strip which is directed parallel to the axis of rotation, and with a static clamping cup for cooperating with the clamping strip, which cup adjoins the hair trap opening and is arranged substantially concentrically relative to the axis of rotation, while the cutting device is located in an edge of the clamping cup adjoining the hair trap opening, and the means for adjusting the clamping force comprise means for displacing the clamping cup relative to the axis of rotation. In this embodiment, the hairs are caught by the elastic clamping strip provided on the rotary carrier and are subsequently clamped in between the clamping strip and the static clamping cup which is fastened to, for example, a housing of the appliance. The rotary movement of the clamping strip along the clamping cup causes the hairs to be carried along by the clamping strip and to be extracted partly from the skin, some slip occurring between the moving clamping strip and the hairs and between the hairs and the static clamping cup. Since the clamping cup is displaceable relative to the axis of rotation, a clamping force between the clamping strip and the clamping cup occurring during the movement of the elastic clamping strip along the clamping cup is adjustable. A comparatively small clamping force leads to comparatively much slip between the clamping strip and the clamped hairs, so that a comparatively short extraction distance is achieved, whereas a comparatively strong clamping force leads to comparatively little slip between the clamping strip and the clamped hairs, so that a comparatively long extraction distance is achieved. Since the cutting device is arranged in an edge of the clamping cup which adjoins the hair trap opening, the hairs extracted partly from the skin are cut through by the cutting device close to the skin, so that a portion of each hair extracted from the skin and cut through is as long as possible.

A further embodiment of an appliance according to the invention is characterized in that the cutting device comprises two dentated cutter blades of equal pitch arranged next to one another and parallel to the axis of rotation, the cutter blade facing away from the axis of rotation being static and the other cutter blade being drivable parallel to the axis of rotation in an oscillatory movement which is synchronized with the rotation of the carrier and of the clamping strip. Since the oscillatory movement of the cutter blade facing the axis of rotation is synchronized with the rotation of the carrier and the clamping strip, the cutting device will cut through the clamped hairs in a predetermined position of the clamping strip relative to the static clamping cup, i.e. at a predetermined extraction distance of the clamping device. The fact that the cutter blades are of equal pitch means that the cutter blades cut simultaneously in all cutting positions of the dentated cutting edges of the cutter blades, so that the cutting function of the cutter blades is synchronized with the rotation of the carrier and of the clamping strip in an identical manner in all cutting positions, and a uniform extraction distance is achieved.

A yet further embodiment of an appliance according to the invention is characterized in that the static cutter blade of the cutting device projects beyond the oscillatory cutter blade of the cutting device at a side which faces the hair trap opening. The partial extraction of the hairs from the skin leads to so-called skin cones around said hairs, which cones will disappear again the moment the hairs are cut through. Since the static cutter blade projects beyond the oscillatory cutter blade at the side facing the hair trap opening, said skin cones are pushed back by the static cutter blade, whereby it is prevented that the skin cones enter between the teeth of the cutter blades and skin damage would arise.

A special embodiment of an appliance according to the invention is characterized in that the hair trap opening is bounded at a side facing away from the cutting device by a skin-tensioning element which extends parallel to the axis of rotation in an imaginary plane extending through the static cutter blade. The use of the skin-tensioning element prevents the skin from coming into contact with the rotary carrier of the clamping device and from becoming clamped in. In addition, the hairs are raised by the skin-tensioning element, so that the hairs can penetrate farther into the hair trap opening and the probability of the hairs being carried along by the rotary carrier of the clamping device is considerably increased.

A further embodiment of an appliance according to the invention is characterized in that the cooperating clamping elements are provided on a carrier which is rotatable about an axis of rotation, the hair trap opening being provided in a flexible cover plate which is provided around the carrier with the cooperating clamping elements and is rotatable about the axis of rotation through a limited angle, while the cutting device comprises a cutter element which is provided on the cover plate adjacent an end of the hair trap opening, as seen in a direction of rotation of the carrier. The hairs penetrating through the hair trap opening are clamped in between the cooperating clamping elements and subsequently extracted partly from the skin under the influence of the rotation of the clamping elements. The rotation of the clamping elements at the same time displaces the hairs in the hair trap opening up to said end of the hair trap opening where the cutter element cutting the clamped hairs is present. Since the hair trap opening and the cutter element are provided on the flexible cover plate which is rotatable about the axis of rotation, the position of the cutter element relative to the clamping device and thus the extraction distance of the clamping device are adjustable in a simple manner through rotation of the cover plate.

A yet further embodiment of an appliance according to the invention is characterized in that the cutter element provided on the cover plate is a cutting edge which bounds the hair trap opening. In this embodiment, the clamped hairs are cut through by said cutting edge under the influence of the rotational movement performed by the cooperating clamping elements with respect to the cover plate. The cutting edge bounding the hair trap opening forms a particularly simple and practical cutter element.

A special embodiment of an appliance according to the invention is characterized in that the cutting device in addition comprises a knife for cooperating with the cutting edge of the hair trap opening, said knife being provided on the carrier immediately behind the cooperating clamping elements, as seen in the direction of rotation of the carrier, and extending parallel to the axis of rotation. Hairs clamped by the cooperating clamping elements in this embodiment are cut through as a result of the cooperation between the cutting edge of the hair trap opening and the rotating knife, so that the cutting function of the cutting device is considerably improved.

A further embodiment of an appliance according to the invention is characterized in that the hair trap opening is a slot in the cover plate which extends in the direction of rotation of the carrier and which has a tapering shape seen in the direction of rotation of the carrier. The tapering shape of the slot extending in the direction of rotation of the carrier provides a high probability of catching hairs, while at the same time damage to the skin caused by the cutting device is avoided as much as possible.

BRIEF DESCRIPTION OF THE DRAWINGS

The invention will be explained in more detail below with reference to the drawing, in which.

DESCRIPTION OF THE PREFERRED EMBODIMENTS

Figure 1A:
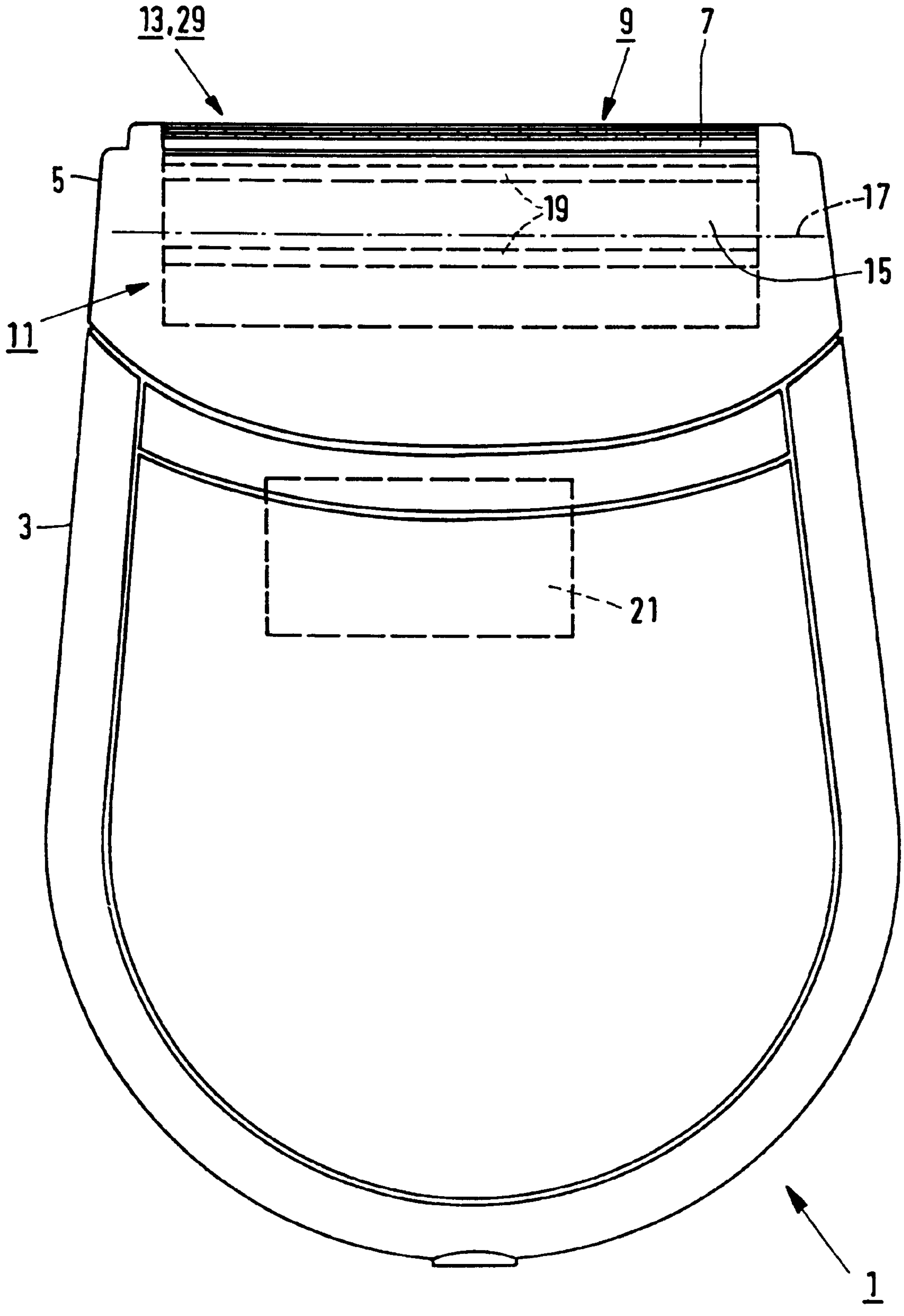
FIG. 1*a* shows a first embodiment of an appliance according to the invention.
Figure 1B:
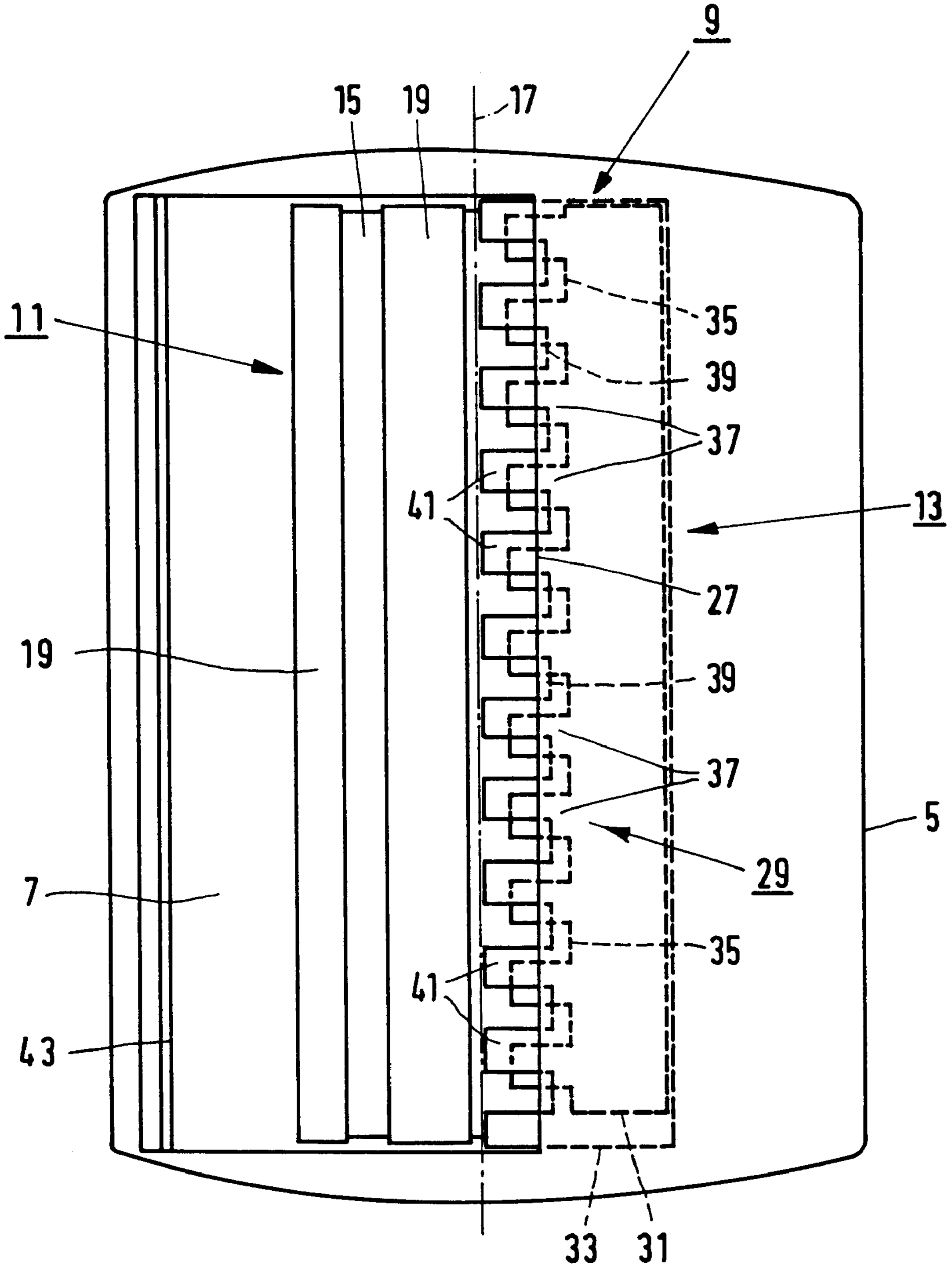
FIG. 1*b* is a plan view of the appliance of FIG. 1*a;*
Figure 2:
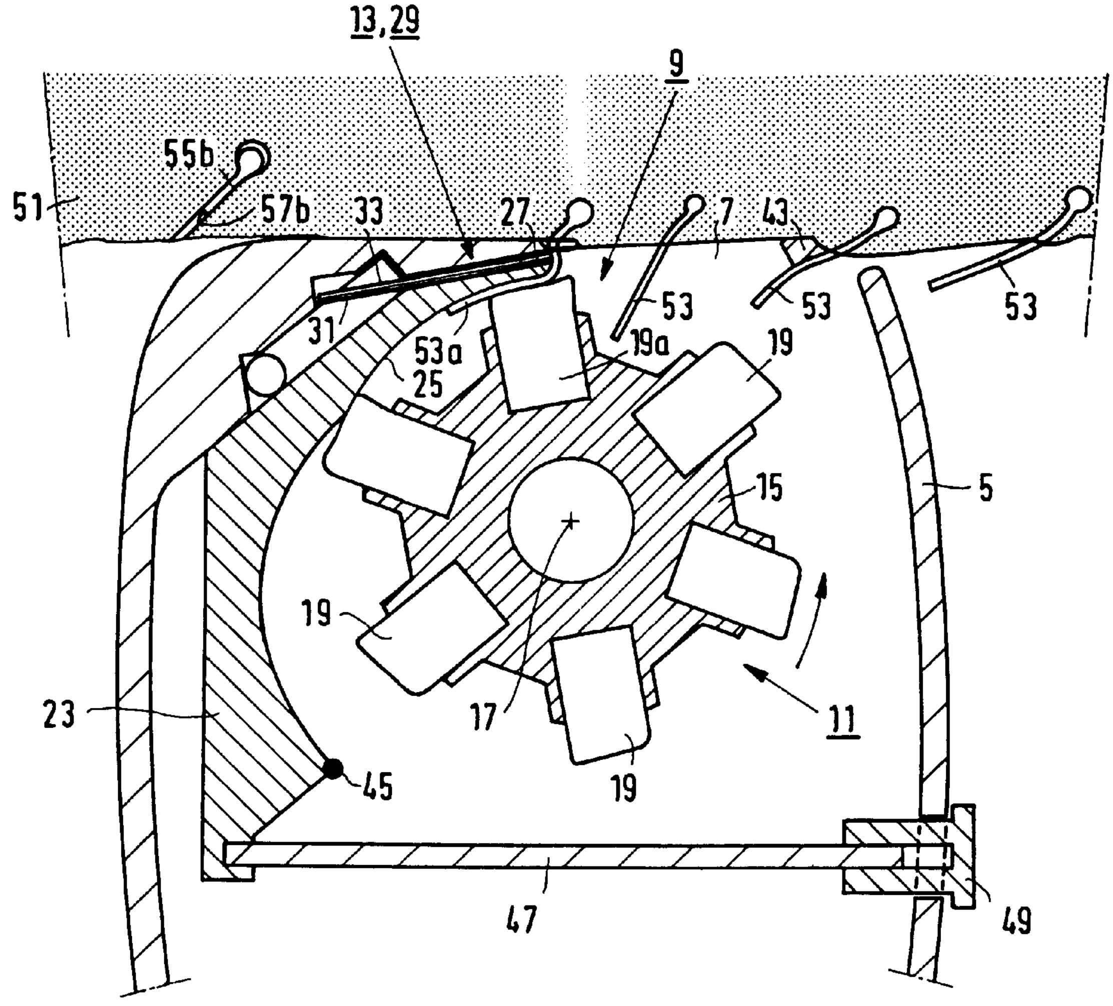
FIG. 2 is a diagrammatic cross-section of a hair removal member of the appliance of FIG. 1*a;*

The first embodiment of an appliance 1 according to the invention as shown in FIGS. 1*a*, 1*b* and 2 is provided with a housing 3 having a hair removal head 5 in which a hair trap opening 7 is provided. A hair removal member 9 to which the skin can be exposed via the hair trap opening 7 for the removal of hairs growing from the skin is present in the hair removal head 5.

As FIGS. 1*b* and 2 show, the hair removal member 9 comprises a clamping device 11 and a cutting device 13. The clamping device 11 comprises a cylindrical metal carrier 15 which is journaled with rotation possibility relative to the housing 3 and to the hair removal head 5 about an axis of rotation 17 which extends parallel to the hair trap opening 7. The carrier 15 has a number of clamping strips 19, for example six such strips, which are provided with equal interspacings on the carrier 15 and which extend parallel to the axis of rotation 17. The clamping strips 19 are made from an elastic material such as, for example, rubber or an elastic synthetic resin. The carrier 15 with the clamping strips 19 is rotatable about the axis of rotation 17 by means of an electric motor 21, which is shown diagrammatically in FIG. 1*a*, via a mechanical transmission which is not shown in the Figures and which is usual and known per se.

As FIG. 2 shows, the clamping device 11 further comprises a metal or synthetic resin clamping cup 23 which is to cooperate with the clamping strips 19. As will be explained further below, the clamping cup 23 occupies an adjustable static position relative to the housing 3 and the hair removal head 5. The clamping cup 23 is provided with a clamping surface 25 which coincides with an imaginary circular cylinder which is arranged substantially concentrically around the axis of rotation 17. The clamping cup 23 and the clamping surface 25 are bounded by a rounded edge 27 which adjoins the hair trap opening 7. When the carrier 15 with the clamping strips 19 is driven by the motor 21 in the direction indicated with an arrow in FIG. 2 during operation, the clamping strips 19 will slide over the clamping surface 25 one after the other as shown in FIG. 2.

As FIGS. 1*b* and 2 further show, the cutting device 13 comprises a so-called hair trimmer 29 which is provided with two cutter blades 31 and 33 which are arranged next to one another and parallel to the axis of rotation 17 of the carrier 15 and which are present in the clamping cup 23. As FIG. 1*b* shows, a side 35 facing the hair trap opening 7 and belonging to the cutter blade 31 facing the carrier 15 is provided with cutting teeth 37, while a side 39 facing the hair trap opening 7 and belonging to the cutter blade 33 remote from the carrier 15 is provided with cutting teeth 41. The cutting teeth 37 and 41 have the same pitch and project beyond the edge 27 of the clamping cup 23. The cutter blade 33 at the skin side is static, i.e. it is in a fixed position relative to the housing 3 and the hair removal head 5, whereas the other cutter blade 31 can be made to oscillate parallel to the axis of rotation 17 by means of the motor 21 via a further mechanical transmission which is not shown in the Figures and is usual and known per se. As FIGS. 1*b* and 2 further show, the side 39 of the static cutter blade 33 projects beyond the side 35 of the oscillatory cutter blade 31. The hair trap opening 7 is bounded at a side facing away from the clamping cup 23 by a skin-tensioning element 43 which extends parallel to the axis of rotation 17.

As was noted above, the static position of the clamping cup 23 relative to the housing 3 and relative to the carrier 15 journaled in the housing 3 is adjustable. As FIG. 2 shows, the clamping cup 23 is for this purpose hinged to the housing 3 by means of a hinge pin 45 which extends parallel to the axis of rotation 17. The clamping cup 23 is held in position relative to the housing 3 by means of a pressure rod 47 which is longitudinally displaceable by means of an adjustment nut 49 which can be turned by a user of the appliance 1. The clamping surface 25 of the clamping cup 23 can be displaced over small distances in a substantially radial direction relative to the axis of rotation 17 through a displacement of the pressure rod 47, so that a clamping force obtaining between the clamping surface 25 and the clamping strips 19 is adjustable. Furthermore, the mechanical transmission between the motor 21 and the carrier 15 of the clamping device 11 and the further mechanical transmission between the motor 21 and the oscillatory cutter blade 31 of the cutting device 13 are so constructed that the oscillatory movement of the cutter blade 31 is synchronized with the rotary movement of the carrier 15 with the clamping strips 19, i.e. the cutter blades 31 and 33 of the cutting device 13 will cut a hair present between the cutting teeth 37, 41 whenever the consecutive clamping strips 19 are in a predetermined position relative to the clamping surface 25 of the clamping cup 23. Such a synchronization can be achieved in that a transmission ratio is provided between said mechanical transmissions in a manner which is usual and known per se.

The operation of the appliance 1 is as follows. When the appliance 1 is placed on the skin 51 with the hairs 53 to be removed during operation, the hairs 53 will penetrate the hair trap opening 7 as shown in FIG. 2. A hair 53 which has entered the hair trap opening 7 is first taken along by one of the clamping strips 19 and is subsequently clamped in between the relevant clamping strip 19 and the clamping surface 25 of the clamping cup 23. FIG. 2 shows a hair 53*a* which is clamped in between a clamping strip 19*a* and the clamping surface 25. After the relevant hair 53*a* has been clamped in between the clamping strip 19*a* and the clamping surface 25, the hair will be carried along by the clamping strip 19*a* as a result of the continuing movement of the clamping strip 19*a* relative to the clamping cup 23 and owing to the friction between the hair 53*a* and the clamping strip 19*a*, so that the hair 53*a* is partly extracted from the skin 51. The hair 53*a* has by then been bent over the edge 27 of the clamping cup 23, so that the hair 53*a* is cut through adjacent the skin 51 by the cutting device 13 arranged in the edge 27. After the hair 53*a*, extracted partly from the skin 51, has been cut through adjacent the skin, a non-cut portion of the hair 53*a* will return into the skin, an end of the non-cut portion of the hair 53*a* sinking to below the surface of the skin 51. FIG. 2 shows by way of example a hair 55*b* thus cut through and returned into the skin 51 with an end 57*b*. A smooth shaving result is thus obtained through the cooperation between the clamping device 11 and the cutting device 13. Since it takes some time for the hairs cut through in this manner to grow up to the skin surface level again, the smoothness obtained remains intact during a reasonably long period.

As was discussed above, the hairs are partly extracted from the skin by the clamping device 11 before they are cut through by the cutting device 13. A so-called extraction distance over which the clamping device 11 extracts the hairs from the skin before they are cut through by the cutting device 13 is determined inter alia by the clamping force between the clamping strips 19 and the clamping surface 25 of the clamping cup 23 and by the position of the clamping strips 19 relative to the clamping surface 25 in which the cutting device 13 cuts the clamped hairs, which position follows from the synchronization between the mechanical transmissions mentioned above. Since the clamping force between the clamping strips 19 and the clamping surface 25 can be adjusted by the user of the appliance 1 by means of the adjustment nut 49, said extraction distance can be adjusted by the user. If the user sets a comparatively small clamping force, there will be comparatively much slip between the clamping strips 19 and the hairs clamped in between the clamping strips 19 and the clamping cup 23, so that the hairs will be taken along by the clamping strips 19 to a limited extent only, and a comparatively short extraction distance is achieved. If the user sets a comparatively great clamping force, there will be comparatively little slip between the clamping strips 19 and the hairs clamped in between the clamping strips 19 and the clamping cup 23, so that the hairs will be taken along by the clamping strips 19 over a comparatively long distance, and a comparatively great extraction distance is achieved. As is known, the partial extraction of the hairs from the skin causes a pain sensation which increases with an increasing extraction distance. The user accordingly has a freedom of choice through the use of the adjustable clamping cup 23. The user may set a comparatively great clamping force and extraction distance, whereby a very good smoothness is indeed achieved which in addition remains intact during a comparatively long period, but whereby comparatively much pain is caused by the clamping device 11. The user may alternatively set a comparatively small clamping force and extraction distance, which does cause hardly any pain owing to the clamping device 11, but now the achieved smoothness will be maintained for a comparatively short period only.

It is achieved that all cutting teeth 37, 41 cut simultaneously in that the cutting teeth 37, 41 of the cutter blades 31, 33 of the cutting device 13 have the same pitch, i.e. the cutting teeth 37, 41 all cut when the clamping strips 19 are in a predetermined position relative to the clamping surface 25. A uniform extraction distance is achieved thereby over the entire sides 35, 39 of the cutter blades 31, 33. Since the side 39 of the static cutter blade 33 projects beyond the side 35 of the oscillatory cutter blade 31, it is prevented that so-called skin cones will enter between the cutting teeth 37, 41 of the cutting device 13, which would give rise to skin damage. Such skin cones arise around the hairs which are clamped in by the clamping device 11 and are partly extracted from the skin, and disappear the moment the relevant hairs are cut through. The use of the skin-tensioning element 43 prevents the skin from coming into contact with the rotary carrier 15 and from becoming clamped in between the carrier 15 and the clamping cup 23. Furthermore, hairs lying flat on the skin are raised by the skin-tensioning element 43, so that these hairs will enter the hair trap opening 7 and will be carried along by the carrier 15. The skin-tensioning element 43 preferably extends in an imaginary plane which passes through the static cutter blade 33. An optimum position of the cutting device 13 relative to the skin is obtained in that manner, the cutter blades 31, 33 cutting through the clamped hairs very close to the skin surface.

It is noted that the user of the appliance 1 may alternatively set the clamping cup 23 in a first extreme position in which the clamping force between the clamping strips 19 and the clamping surface 25 is zero or substantially zero. In this position of the clamping cup 23, the extraction distance over which the clamping device 11 extracts the hairs from the skin before they are cut through by the cutting device 13 is negligibly small, so that the appliance 1 functions as a conventional shaver. The user may alternatively set the clamping cup 23 in a second extreme position in which the clamping force between the clamping strips 19 and the clamping surface 25 is so great that the clamped hairs are fully extracted from the skin before the cutting device 13 gets a chance of cutting through the hairs. The appliance 1 thus functions as a conventional depilation appliance in the second extreme position of the clamping cup 23. It is noted that the appliance 1 may also be given a conventional depilation function in that the further mechanical transmission between the motor 21 and the oscillatory cutter blade 31 is provided with a coupling which can be disconnected by the user. In such an alternative embodiment, a conventional depilation function is provided in that the user switches off the cutting device 13 through uncoupling of said further mechanical transmission. The appliance 1 thus has a wide range of utilization possibilities. The user may use the appliance 1, for example, with the clamping cup 23 in its first extreme position for shortening long hairs and subsequently with the clamping cup 23 in its second extreme position for depilating the previously shortened hairs. Furthermore, as noted above, the user may set the clamping cup 23 in an intermediate position between the first and the second extreme position, which provides a deep-shaving function where the user can set a ratio between the quality of the shaving result and the pain level to be experienced.

In the second embodiment of an appliance 101 according to the invention shown in FIGS. 3, 4, 5*a*, 5*b*, and 5*c*, a housing 103 is provided with a hair removal head 105 in which hair trap openings 107 are provided. In the hair removal head 105 there is a hair removal member 109 to which skin can be exposed through the hair trap openings 107 for the removal of hairs growing from this skin.

Figure 3:
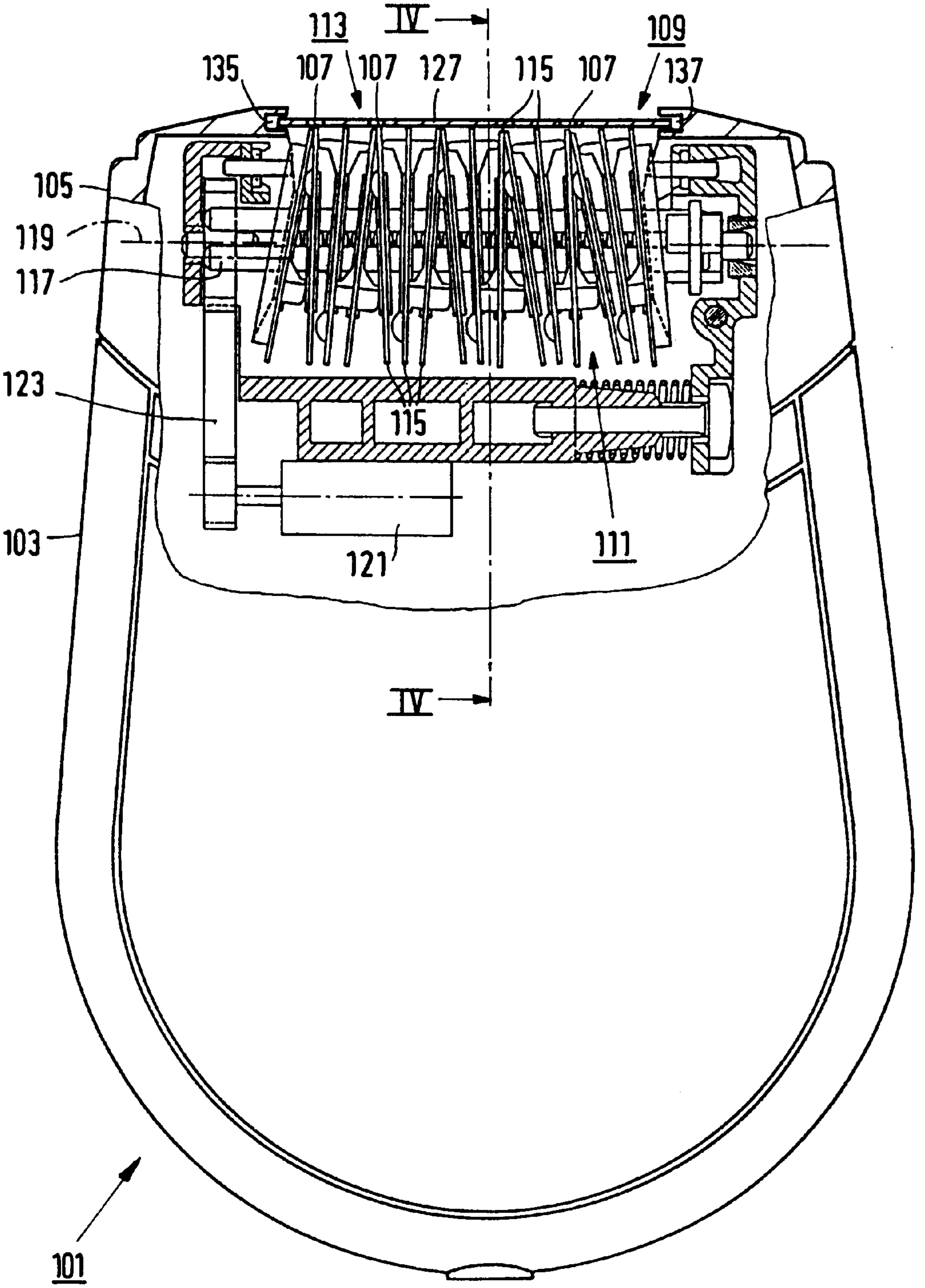
FIG. 3 is a diagrammatic cross-section of a second embodiment of an appliance according to the invention.
Figure 4:
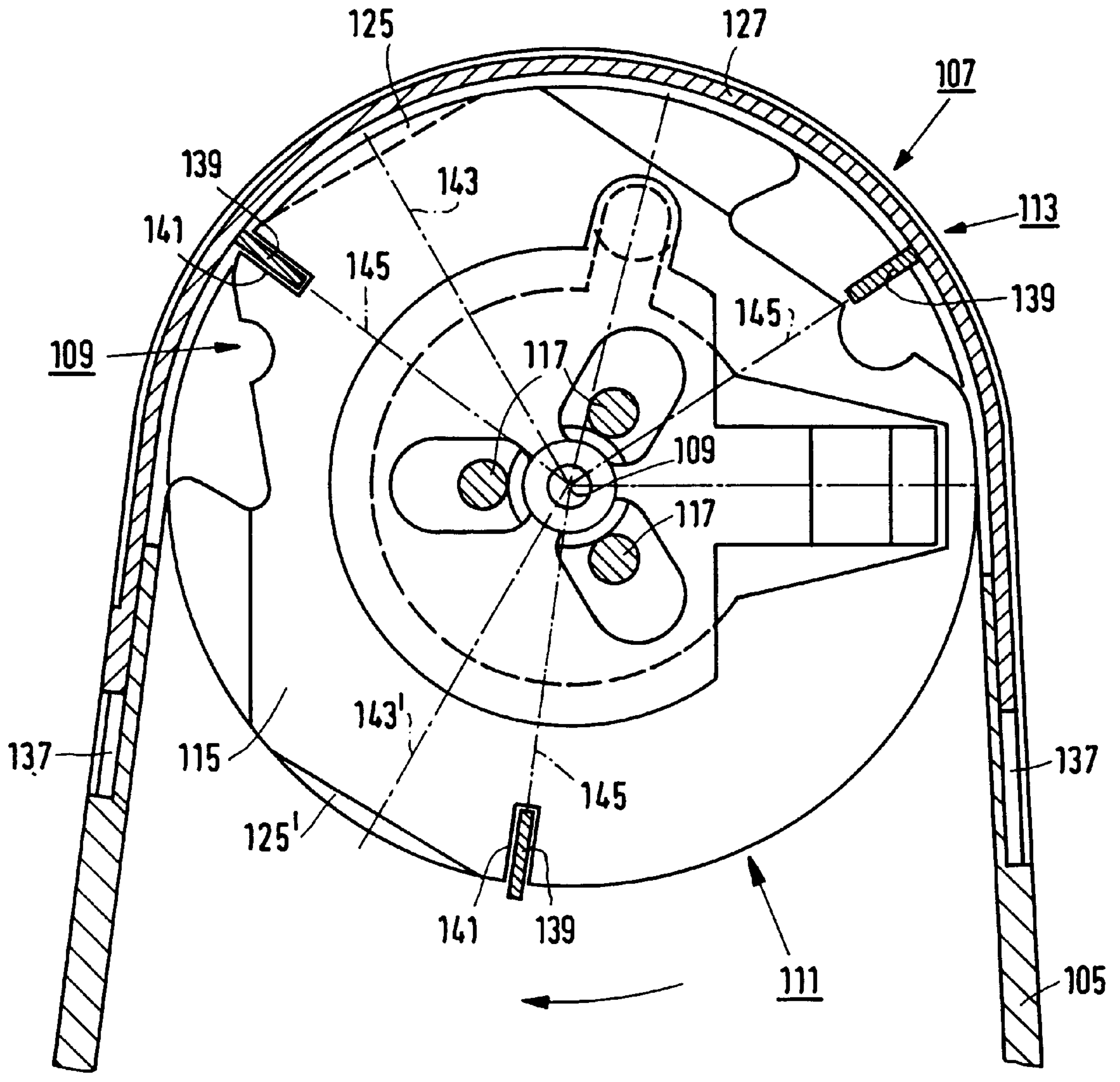
FIG. 4 is a diagrammatic cross-section taken on the line IV—IV in FIG. 3.

As FIGS. 3 and 4 show, the hair removal member 109 comprises a clamping device 111 and a cutting device 113. The clamping device 111 comprises a number of cooperating metal clamping discs 115 which are coupled to a drive shaft 117 which can be rotated about an axis of rotation 119 and can be driven by an electric motor 121 via a mechanical transmission 123. The clamping discs 115 are each pivotable relative to the drive shaft 117 about a pivot axis which is perpendicular to the axis of rotation 119. The construction and operation of the clamping device 111 with the rotatable and pivotable clamping discs 115 correspond substantially to the construction and operation of a depilation head with rotatable and pivotable clamping discs as known from European Patent EP-B-0 532 106. The construction and operation of the clamping device 111 described in EP-B-0 532 106 are accordingly deemed to be incorporated in the contents of the present Patent Application. The clamping discs 115 cooperate in pairs, hairs exposed to the clamping device 111 through the hair trap openings 107 being clamped between clamping surfaces 125 of a pair of clamping discs 115 positioned next to one another through pivoting of said clamping discs 115 into a clamping position in which said clamping discs 115 bear on one another with their clamping surfaces 125 while exerting a clamping force. The clamped hairs are subsequently partly extracted from the skin by the continuing rotary movement of the cooperating clamping discs 115 relative to the hair trap openings 107.

Figure 5A:
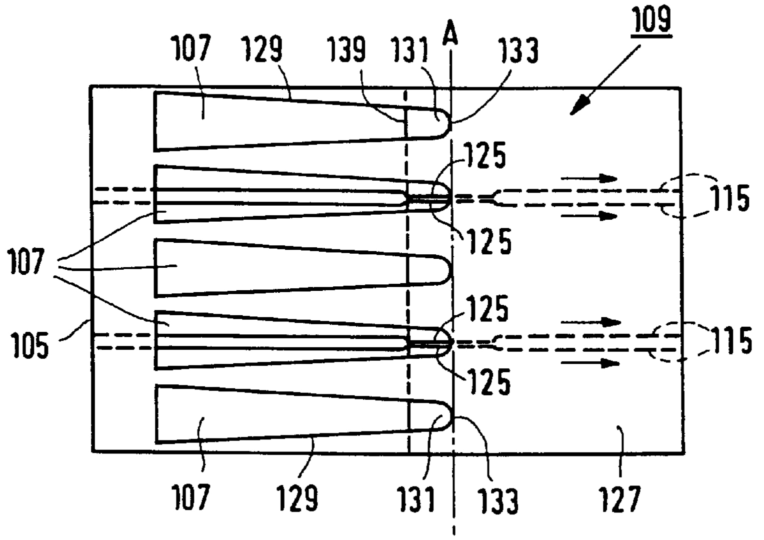
FIG. 5*a* is a plan view of the appliance of FIG. 3, a cover plate of the appliance being in a first end position here.
Figure 5B:
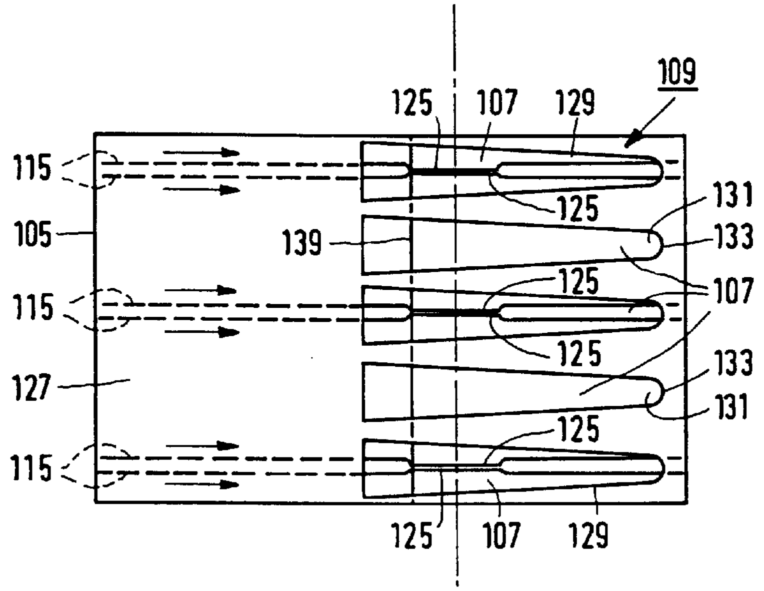
FIG. 5*b* is a plan view of the appliance of FIG. 3, the cover plate of the appliance now being in a second end position.
Figure 5C:
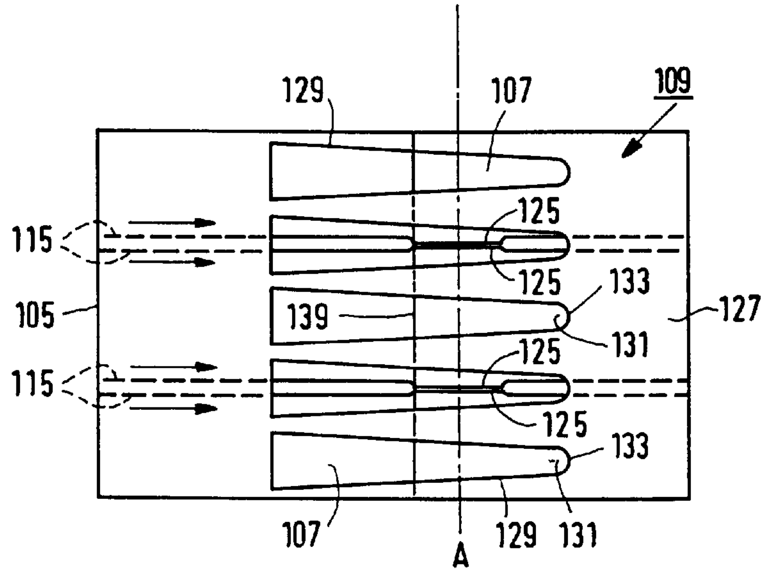
FIG. 5*c* is a plan view of the appliance of FIG. 3, the cover plate of the appliance being in an intermediate position.

As FIGS. 3 and 4 further show, the cutting device 113 comprises a flexible metal cover plate 127 which is provided around the drive shaft 117 carrying the cooperating clamping discs 115. As is most clearly shown in FIGS. 5*a*, 5*b*, and 5*c*, said hair trap openings 107 are provided in the cover plate 127 which has a separate hair trap opening 107 in the form of a slot 129 in the cover plate 127 extending in the direction of rotation of the clamping discs 115 for each pair of cooperating clamping discs 115 situated next to one another. The slots 129 have a tapering shape seen in the direction of rotation of the clamping discs 115. A cutting edge 133 defining an end 131 of the slot 129 is present near said end 131 of each slot 129, as seen in the direction of rotation of the clamping discs 115. It is noted that the number of slots 129 and clamping discs 115 shown in FIGS. 5*a*, 5*b*, and 5*c* is reduced for the sake of simplicity compared with the number shown in FIG. 3.

As FIG. 3 further shows, the cover plate 127 is enclosed in a direction parallel to the axis of rotation 119 between a first groove 135 in the housing 103 and a second groove 137 in the housing 103. As FIG. 4 shows, the grooves 135 and 137 extend around the ends of the drive shaft 117, so that the cover plate 127 is guided with shifting possibility in the grooves 135 and 137 and can be rotated through a limited angle about the drive shaft 117 and the axis of rotation 119 by the user of the appliance 101. The effect achieved by a rotation of the cover plate 127 will be explained further below.

As FIGS. 4, 5*a*, 5*b*, and 5*c* show, the cutting device 113 further comprises a number of knives 139 extending parallel to the axis of rotation 119 and designed to cooperate with the cutting edges 133 of the slots 129. The knives 139 are not shown in FIG. 3 for the sake of simplicity. The knives 139 extend along substantially the entire drive shaft 117 and are individually enclosed in respective consecutive recesses 141 provided in the consecutive clamping discs 115 on an imaginary line directed parallel to the axis of rotation 119. Seen in the direction of rotation of the clamping discs 115, each knife 139 is positioned immediately behind the cooperating clamping surfaces 125 of the clamping discs 115. As is described in EP-B-0 532 106, each clamping disc 115 has two clamping surfaces 125 and 125' which lie on two radii 143 and 143' of the clamping disc 115 which enclose an angle of 120° with one another. EP-B-0 532 106 further describes how the identical clamping discs 115 are fastened on the drive shaft 117 such that the consecutive clamping discs 115 are mutually rotated through an angle of 120° each time about the drive shaft 117. As a result of this, the cutting device 113 is provided with three knives 139 which lie on three radii 145 of the clamping discs 115 enclosing angles of 120° with one another.

The operation of the appliance 101 is explained below with reference to FIGS. 5*a*, 5*b*, and 5*c*. In FIG. 5*a*, the cover plate 127 is in a first end position in which the appliance 101 acts as a conventional shaver, as is explained below. In FIG. 5*b*, the cover plate 127 is in a second end position in which the appliance 101 has a conventional depilation function. In FIG. 5*c*, the cover plate 127 is in an intermediate position between the first and the second end position, the appliance 101 now having a deep-shaving function. The FIGS. 5*a*, 5*b*, and 5*c* each show a situation in which a number of pairs of clamping discs 115 situated next to one another have just entered the clamping position owing to a pivoting of the clamping discs 115, hairs previously penetrated through the hair trap openings 107 being clamped in between the clamping surfaces 125 of the cooperating clamping discs 115. This position of the clamping discs 115 is a reference position indicated in FIGS. 5*a*, 5*b*, and 5*c* by means of the reference line A—A.

In the intermediate position of the cover plate 127 shown in FIG. 5*c*, the clamped hairs are subsequently partly extracted from the skin by the continuing rotational movement performed by the cooperating clamping discs 115 relative to the hair trap openings 107. When the clamping surfaces 125 with the hairs clamped in between them subsequently reach the cutting edges 133 of the hair trap openings 107, the hairs previously extracted partly from the skin are cut through by the cooperation of the knife 139 adjoining the clamping surfaces 125 and the cutting edges 133. The appliance 101 with the cover plate 127 in the intermediate position shown thus has a deep-shaving function, the hairs being extracted from the skin over a certain extraction distance by the clamping device 111 before the hairs are cut through adjacent the skin by the cutting device 113. A smooth shaving result which remains intact during a long period is achieved thereby, as was explained above with reference to the appliance 1.

The extraction distance over which the clamping device 111 extracts the hairs from the skin before they are cut through by the cutting device 113 is adjustable through rotation of the cover plate 127 about the clamping discs 115. A rotation of the cover plate 127 changes a position of the cutting edges 133 of the cutting device 113 relative to the clamping device 111 and the reference line A—A. If the cover plate 127 is rotated from the intermediate position shown in FIG. 5*c* in the direction of rotation of the clamping discs 115, the distance between the cutting edges 133 and the reference line A—A is increased, so that also the extraction distance is increased. The removal of the hairs as a result causes more pain then, but the achieved smoothness is maintained during a longer period because the cut hairs sink back more deeply below the skin surface. If the cover plate 127 is rotated from the intermediate position shown in FIG. 5*c* in a direction opposed to the direction of rotation of the clamping discs 115, the distance between the cutting edges 133 and the reference line A—A is reduced, so that also the extraction distance is reduced. Hair removal is less painful as a result, but the achieved smoothness will remain intact during a shorter period because the cut hairs will retract less deeply below the skin surface level.

In the first end position of the cover plate 127 shown in FIG. 5*a*, the cutting edges 133 are approximately on the reference line A—A. With the cover plate 127 in this position, the hairs are clamped in between the clamping surfaces 125 of the cooperating clamping discs 115 and almost immediately afterwards cut through as a result of the cooperation between the cutting edges 133 and the knife 139. The clamped hairs are accordingly not or substantially not extracted from the skin before the hairs are cut when the cover plate 127 is in this position, so that the appliance 101 has a conventional shaving function with the cover plate 127 in this position. It is noted that such a conventional shaving function is also achieved when the first end position of the cover plate 127 is such that the cutting edges 133 are present in front of the reference line A—A, seen in the direction of rotation of the clamping discs 115. The hairs are not clamped in between the clamping discs 115 then, but are immediately cut through as a result of the cooperation between the cutting edges 133 and the knife 139. It is further noted that the cutting device 113 of the appliance 101 may also have a cutting function without being provided with the knives 139 if the cutting edges 133 are present on the reference line A—A with the cover plate 127 in the first end position, or lie immediately behind the reference line A—A seen in the direction of rotation of the clamping discs 115. In such an alternative embodiment of the appliance 101, the hairs clamped in between the clamping surfaces 125 of the cooperating clamping discs 115 are taken along in rotation by the clamping discs 115 and cut through by the cutting edges 133.

The distance between the cutting edges 133 and the reference line A—A in the second end position of the cover plate 127 shown in FIG. 5*b* is so great that the hairs clamped between the clamping surfaces 125 of the cooperating clamping discs 115 are completely extracted from the skin before the clamped hairs reach the cutting edges 133. The appliance 101 has a conventional depilation function with the cover plate 127 in this position.

The tapering shape of the slots 129 of the hair trap openings 107 seen in the direction of rotation of the drive shaft 117 and their resulting small width adjacent the cutting edges 133 prevent as much as possible that the skin can penetrate the hair trap openings 107 adjacent the cutting edges 133 and can become damaged by the cutting edges 133 or the cutting edges 133 and the knife 139. The comparatively great width of the slots at the sides remote from the cutting edges 133 provides a high hair-catching probability.

The clamping device 11 of the appliance 1 described above comprises a rotary carrier 15 with clamping strips 19 and a clamping cup 23 which is to cooperate with the clamping strips 19, whereas the clamping device 111 of the appliance 101 described above comprises a rotary drive shaft 117 with clamping discs 115. It is noted that an appliance according to the invention may also be provided with an alternative type of clamping device with at least one clamping element which is movable relative to a hair trap opening of the appliance or an alternative type of clamping device with at least one pair of mutually cooperating clamping elements which are movable relative to a hair trap opening of the appliance. Thus, for example, cooperating clamping blocks may be used instead of the clamping strips 19 in the appliance 1, which blocks are movable relative to the carrier 15 in a direction parallel to the axis of rotation 17. An alternative type of rotatable support may for example be used instead of the drive shaft 117 with the pivotable clamping discs 115 in the appliance 101, which support is provided with clamping blocks which are movable relative to the support in a direction parallel to an axis of rotation of the support.

The cutting device 13 of the appliance 1 described earlier comprises a hair trimmer 29, while the cutting device 113 of the appliance 101 discussed above has a number of cutting edges 133 which are to cooperate with a number of rotary knives 139. It is noted that an appliance according to the invention may be provided with an alternative type of cutting device. Thus, for example, a single oscillatory shaving cutter may be used instead of the hair trimmer 29 in the appliance 1. Furthermore, the static cutter blade 33 may be so provided in the appliance 1 that the static cutter blade 33 lies directly against the skin during use. In the appliance 101, for example, a different type of cutter element may be provided on the cover plate 127 to replace the cutting edges 133, such as a shaving knife which extends parallel to the drive shaft 117.

The extraction distance in the appliance 1 discussed above over which the clamping device 11 extracts the hairs from the skin before they are cut through by the cutting device 13 is adjustable through an adjustment of the clamping force with which the clamping device 11 clamps the hairs, while in the appliance 101 the extraction distance is adjustable through adjustment of a position of the cutting edges 133 of the cutting device 113 relative to the clamping device 111. It is finally noted that an appliance according to the invention may be provided with means for adjusting the extraction distance which are of an alternative type. Thus, for example, the means 45, 47, 49 for adjusting the clamping force of the clamping device 11 in the appliance 1 may be replaced by means for adjusting the synchronization between the rotary movement of the carrier 15 of the clamping device 11 and the oscillatory movement of the cutter blade 31 of the cutting device 13. A position occupied by the clamping strips 19 relative to the clamping surface 25 at the moment when the cutting device 13 cuts through the hairs clamped in between the clamping strips 19 and the clamping surface 25 is adjustable by such alternative means, said position being a measure for the extraction distance.

We claim:

1. An appliance for the removal of hairs growing from skin, which appliance is provided with a clamping device comprising clamping strips and a clamping surface for clamping a hair and subsequently extracting the hair at least partly from the skin, and with a cutting device with cutting edges for cutting through, adjacent the skin, of a hair which has been partly extracted from the skin, wherein the appliance is provided with at least one means for adjusting an extraction distance over which the clamping device extracts the hair from the skin before the cutting device cuts through the hair, the at least one adjusting means being selected from the group consisting of (a) means for adjustment of a position of the cutting edges of the cutting device relative to the clamping device, (b) means for adjusting the synchronization between rotary movement of a carrier of the clamping device and oscillatory movement of a cutter blade of the cutting device; and (c) means for adjustment of a position occupied by the clamping strips relative to the clamping surface at the moment when the cutting device cuts through the hairs clamped in between the clamping strips and the clamping surface, and combinations thereof.

2. An appliance as claimed in claim 1, characterized in that the at least one means for adjusting the extraction distance is adjustable at least to a first setting in which the extraction distance is zero or substantially zero and to a second setting in which the clamping device extracts the hairs completely from the skin.

3. An appliance as claimed in claim 1, characterized in that the clamping device comprises at least one clamping element which is movable relative to a hair trap opening of the appliance, the at least one means for adjusting the extraction distance comprising means for adjusting a clamping force with which the clamping device clamps the hair.

4. An appliance as claimed in claim 1, wherein said at least one means for adjusting an extraction distance over which the clamping device extracts the hair from the skin before the cutting device cuts through the hair consists of means for adjustment of a position of the cutting edges of the cutting device relative to the clamping device.

5. An appliance as claimed in claim 1, wherein said at least one means for adjusting an extraction distance over which the clamping device extracts the hair from the skin before the cutting device cuts through the hair consists of means for adjusting the synchronization between the rotary movement of a carrier of the clamping device and the oscillatory movement of a cutter blade of the cutting device.

6. An appliance as claimed in claim 1, wherein said at least one means for adjusting an extraction distance over which the clamping device extracts the hair from the skin before the cutting device cuts through the hair consists of means for adjustment of a position occupied by the clamping strips relative to the clamping surface at the moment when the cutting device cuts through the hairs clamped in between the clamping strips and the clamping surface.

7. An appliance for the removal of hairs growing from skin, which appliance is provided with a clamping device for clamping a hair and subsequently extracting the hair at least partly from the skin, and with a cutting device for cutting through, adjacent the skin, of a hair which has been partly extracted from the skin, wherein the appliance is provided with means for adjusting an extraction distance over which the clamping device extracts the hair from the skin before the cutting device cuts through the hair, which clamping device comprises at least one pair of cooperating clamping elements which are movable relative to a hair trap opening of the appliance, the means for adjusting the extraction distance comprising means for adjusting a position of the cutting device relative to the clamping device.

8. An appliance as claimed in claim 7, wherein the cooperating clamping elements are provided on a carrier which is rotatable about an axis of rotation, the hair trap opening being provided in a flexible cover plate which is provided around the carrier with the cooperating clamping elements and is rotatable about the axis of rotation through a limited angle, while the cutting device comprises a cutter element which is provided on the cover plate adjacent an end of the hair trap opening, as seen in a direction of rotation of the carrier.

9. An appliance as claimed in claim 8, wherein the cutter element provided on the cover plate is a cutting edge which bounds the hair trap opening.

10. An appliance as claimed in claim 9, wherein the cutting device in addition comprises a knife for cooperating with the cutting edge of the hair trap opening, said knife being provided on the carrier immediately behind the cooperating clamping elements, as seen in the direction of rotation of the carrier, and extending parallel to the axis of rotation.

11. An appliance as claimed in claim 8, wherein the hair trap opening is a slot in the cover plate which extends in the direction of rotation of the carrier and which has a tapering shape seen in the direction of rotation of the carrier.

12. An appliance for the removal of hairs growing from skin, which appliance is provided with a clamping device for clamping a hair and subsequently extracting the hair at least partly from the skin, and with a cutting device for cutting through, adjacent the skin, of a hair which has been partly extracted from the skin, wherein the appliance is provided with means for adjusting an extraction distance over which the clamping device extracts the hair from the skin before the cutting device cuts through the hair, the clamping device comprises at least one clamping element which is movable relative to a hair trap opening of the appliance, the means for adjusting the extraction distance comprises means for adjusting a position of the cutting device relative to the clamping device and means for adjusting a clamping force with which the clamping device clamps the hair, the clamping device is provided with a carrier which is rotatable about an axis of rotation directed parallel to the hair trap opening and which is provided with an elastic clamping strip which is directed parallel to the axis of rotation, and with a static clamping cup for cooperating with the clamping strip, which cup adjoins the hair trap opening and is arranged substantially concentrically relative to the axis of rotation, the cutting device being located in an edge of the clamping cup adjoining the hair trap opening, and the means for adjusting the clamping force comprises means for displacing the clamping cup relative to the axis of rotation.

13. An appliance as claimed in claim 12 wherein the cutting device comprises two dentated cutter blades of equal pitch arranged next to one another and parallel to the axis of rotation, one said cutter blade facing away from the axis of rotation being static and the other said cutter blade being drivable parallel to the axis of rotation in an oscillatory movement which is synchronized with the rotation of the carrier and of the clamping strip.

14. An appliance as claimed in claim 6, wherein the static cutter blade of the cutting device projects beyond the oscillatory cutter blade of the cutting device at a side which faces the hair trap opening.

15. An appliance as claimed in claim 13, wherein the hair trap opening is bounded at a side facing away from the cutting device by a skin-tensioning element which extends parallel to the axis of rotation in an imaginary plane extending through the static cutter blade.

* * * * *